US008097261B2

(12) United States Patent
Elsemore et al.

(10) Patent No.: US 8,097,261 B2
(45) Date of Patent: Jan. 17, 2012

(54) ROUNDWORM COPROANTIGEN DETECTION

(75) Inventors: David Allen Elsemore, South Portland, ME (US); Laurie A. Flynn, Raymond, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 0 days.

(21) Appl. No.: 12/814,207

(22) Filed: Jun. 11, 2010

(65) Prior Publication Data

US 2010/0248217 A1 Sep. 30, 2010

Related U.S. Application Data

(63) Continuation of application No. 11/763,592, filed on Jun. 15, 2007, now Pat. No. 7,736,660.

(51) Int. Cl.
*A61K 39/00* (2006.01)
*A61K 39/38* (2006.01)
*G01N 33/53* (2006.01)

(52) U.S. Cl. .............. 424/265.1; 424/130.1; 424/141.1; 424/151.1; 424/184.1; 435/7.1; 435/7.2; 435/287.1

(58) Field of Classification Search ............... 424/130.1, 424/141.1, 151.1, 184.1, 265.1; 435/7, 7.1, 435/287.1

See application file for complete search history.

(56) References Cited

U.S. PATENT DOCUMENTS

| | | | |
|---|---|---|---|
| 4,322,495 | A | 3/1982 | Kato |
| 4,789,631 | A | 12/1988 | Maggio |
| 4,839,275 | A | 6/1989 | Weil |
| 4,978,504 | A | 12/1990 | Nason |
| 5,078,968 | A | 1/1992 | Nason |
| 5,238,649 | A | 8/1993 | Nason |
| 5,266,266 | A | 11/1993 | Nason |
| 5,726,010 | A | 3/1998 | Clark |
| 5,843,706 | A | 12/1998 | Cobon et al. |
| 6,057,166 | A | 5/2000 | Childs et al. |
| 6,391,569 | B1 | 5/2002 | Grieve et al. |
| 6,596,502 | B2 | 7/2003 | Lee |
| 7,303,752 | B2 | 12/2007 | Hotez et al. |
| 2002/0132270 | A1 | 9/2002 | Lee |
| 2003/0129680 | A1 | 7/2003 | O'Connor |
| 2004/0214244 | A1 | 10/2004 | Tonelli et al. |

FOREIGN PATENT DOCUMENTS

| | | |
|---|---|---|
| WO | WO 98/12563 | 3/1998 |
| WO | WO 02/075313 | 9/2002 |
| WO | WO 2004/097412 | 11/2004 |

OTHER PUBLICATIONS

Abdel-Rahman, et al., "Evaluation of a diagnostic monoclonal antibody-based capture enzyme-linked immunosorbent assay for detection of a 26-to 28-kd *Fasciola hepatica* coproantigen in cattle" *American Journal of Veterinary Research*, vol. 59, pp. 533-537 (1998).
Bungrio, et al., "Detection of Excretory/Secretory Coproantigens in Hookworm infection", *Am. J. Trop. Med. Hyg.*, vol. 73, No. 5, pp. 915-920 (2005).
Bungrio, et al., "Purification and Molecular Cloning of and Immunization with Anyclostoma ceylancium Excretory-Secretory Protein 2, an Immunocreative Protein Produced by Adult Hookworms", *Infection and Immunity*, vol. 72, No. 4, pp. 2203-2213 (2004).
Carleton, et al., "Prevalence of *Dirofilaria immitis* and gastrointestinal helminths in cats euthanized at animal control agencies in northwest Georgia", *Veterinary Parisitology*, vol. 119, pp. 319-326 (2004).
Coulaud, et al., Albendazole: a new single anthelmintic. Study in 1455 patients, *Acta Tropica*, vol. 41, pp. 87-90 (1984).
De Oliveira, et al., IgM-ELISA for diagnosis of schistosomiasis mansoni in low endemic areas, Cadernos de saúde pública/ Ministério da Saúde, Fundacao Oswaldo Cruz, Escola National de Saúde Pública. vol. 19. pp. 255-261 (2003).
Deplazes, et al., "Detection of Taenia hydatigena copro-antigens by ELISA in dogs", *Veterinary Parisitology*, vol. 36, pp. 91-103 (1990).
Dumenigo, et al., Kinetics of antibody-based antigen detection in serum and faeces of sheep experimentally infected with *Fasciola hepatica*, *Veterinary Parisitology*, vol. 86, pp. 23-31 (1999).
Foreyt, et al., *Veterinary Parasitology Reference Manual, Fifth Edition*, 2001 ISBN 0-8138-2419-2.
Hill, et al., "A Trichuris specific diagnostic antigen from culture fluids of Trichuris suis adult worms", *Veterinary Parasitology*, vol. 68, pp. 91-102 (1997).
IDEXX Laboratories Canine Paravovirus Antigen Test Kit package insert.
Martinez-Maya, et al., Taeniosis and detection of antibodies against Cysticeri among inhabitants of a rural community in Guerro State, Mexico, Salúd Publica de Mexico, vol. 45, pp. 84-89 (2003).
Ott, et al., Demonstration of both Immunologically unique and common antigenic determinants in Dirofilari Immitis and *Toxocara canis* using monoclonal antibodies, *Veterinary Immunology and Immunopathology*, vol. 10, pp. 147-153 (1985).
Roberts, et al., Foundations of Parasitology, Fifth Edition, Library of Congress Card Catalog No. 94-72939, ISBN 0-687-26071-S (1996).
Southworth, Exine development in *Gerbera jamesonii* (Asteraceae: Mutisieae), *American Journal of Botany*, vol. 70, pp. 1038-1047 (1983).

(Continued)

*Primary Examiner* — Rodney P. Swartz
(74) *Attorney, Agent, or Firm* — McDonnell Boehnen Hulbert & Berghoff LLP

(57) ABSTRACT

A composition, device, kit and method for detecting the presence or absence of roundworm in a fecal sample. The composition, device, kit and method of the present invention may be used to confirm the presence or absence of roundworm in a fecal sample from a mammal that may also be infected with one or more of hookworm, whipworm, and heartworm.

25 Claims, 8 Drawing Sheets

OTHER PUBLICATIONS

Willard, et al., "Diagnosis of Aelurostrongylus abstrusus and Dirofilar immitis infections in cats from a human shelter", *Journal of the American Veterinary Medical Association*, vol. 192, pp. 913-916 (1988).

Yamasaki, et al., "Development of Highly Specific Recombinant *Toxocara canis* Second-Stage Larva Excretory-Secretory Antigen for Immunodiagnosis for Human Toxocariasis", *Journal of Clinical Microbiology*, vol. 38, No. 4, pp. 1407-1413 (2000).

Bailey, "The Raising of a Polyclonal Antiserum to a Protein", Methods Mol. Biol., vol. 32, pp. 381-388, (1994).

Barker, et al., "Isolation of a gene family that encodes the porin-like proteins from the human parasitic nematode *Trichuris trichiura*", Gene, vol. 229, pp. 131-136, (1999).

Dean, "Preparation and Characterization of Monoclonal Antibodies to Proteins and Other Cellular Components", Methods Mol. Biol., vol. 32, pp. 361-379, (1994).

Dean, "Preparation and Testing of Monoclonal Antibodies to Recombinant Proteins", Methods Mol. Biol., vol. 80, pp. 23-37, (1998).

Drenckhahn, et al., "Production of Polyclonal Antibodies against Proteins and Peptides", Methods Cell Biol., vol. 37, pp. 7-56, (1993).

Dryden, et al., "Comparison of Common Fecal Flotation Techniques for the Recovery of Parasite Eggs and Oocysts", Vet. Ther., vol. 6, No. 1, pp. 15-28, (2005).

Gullick, "Production of Antisera to Synthetic Peptides", Methods Mol. Biol., vol. 32, pp. 389-399, (1994).

Kennedy, "The Nematode Polyprotein Allergens/Antigens", Parasitol. Today, vol. 16, No. 9, pp. 373-380, (2000).

Morrison, "In Vitro Antibodies: Strategies for Production and Application", Annu. Rev. Immunol., vol. 10, pp. 239-265, (1992).

NCBI Blast: SEQ ID No. 4. Dated Aug. 27, 2009.

Prociv et al., "Human enteric infection with *Ancyostoma caninum*: hookworms reappraised in the light of a "new" zoonosis", Acta. Tropica., vol. 62, pp. 23-44, (1996).

Wright, et al., "Genetically Engineered Antibodies: Progress and Prospects", Crit. Rev. Immunol., vol. 12 (3-4), pp. 125-168, (1992).

Xia, et al., "The ABA-1 allergen of *Ascaris lumbricoides*: sequence polymorphism stage and tissue-specific expression, lipid binding function and protein biophysical properties", Parasitology, vol. 120 (Pt.2), pp. 211-224, (2000).

Yahiro, et al., "Identification, characterization and expression of Toxocara canis nematode polyprotein allergen TBA-1", Parasite Immunol., vol. 20, No. 8, pp. 351-357, (1998).

Voller, "The Enzyme Linke Immunosorbent Assay," Diagnostic Horizon, vol. 2, No. 1, pp. 1-7, Feb. 1978.

Bungiro and Cappello, "Detection of Excretory/Secretory Coproantigens in Hookworm infection," (2005), Am. J. Trop. Med. Hyg. 73(5):915-920.

Hill et al., "A Trichuris specific diagnostic antigen from culture fluids of Trichuris suis adult worms," (1997), Veterinary Parasitology 68:91-102.

Yamasaki et al., "Development of Highly Specific Recombinant Toxocara can's Second-Stage Larva Excretory-Secretory Antigen for Immunodiagnosis of Human Toxocariasis," (2000), Journal of Clinical Microbiology 38 (4):1409-1413.

Bungiro, Jr., et al., "Purification and Molecular Cloning of and Immunization with Ancylostoma ceylancium Excretory-Secretory Protein 2, an Immunoreactive Protein Produced by Adult Hookworms," (2004), Infection and Immunity 72 (4):2203-2213.

Deplazes et al., Detection of Taenia hydatigena copro-antigens by ELISA in dogs, Veterinary Parisitology 36:91-103 (1990).

Ott et al., Demonstration of both immunologically unique and common antigenic determinants in *Dirofilaria immitis* and Toxocara can's using monoclonal antibodies, Veterinary Immunology and Immunopathology 10:147-153 (1985).

Abdel-Rahman at al., Evaluation of a diagnostic monoclonal antibody-based capture enzyme-linked immunosorbent assay for detection of a 26- to 28-kd *Fasciola hepatica* coproantigen in cattle, American Journal of Veterinary Research 59:533-537 (1998).

Martinez-Maya et al., Taeniosis and detection of antibodies against Cysticeri among inhabitants of a rural community in Guerro State, Mexico, Ss.lid Publica de Mexico 45:84-89 (2003).

Dumenigo et al., Kinetics of antibody-based antigen detection in serum and faeces of sheep experimentally infected with *Fasciola hepatica*, Veterinary Parisitology 86:23-31 (1999).

Vvillard et al., Diagnosis of *Aelurostrongylus abstrusus* and *Dirofilaria immitis* infections in cats from a human shelter, Journal of the American Veterinary Medical Association 192:913-916 (1988).

De Oliveira et al., IgM-ELISA for diagnosis of schistosomiasis mansoni in low endemic areas, Cadernos de sat:tde pCiblica / Ministerio da SaCtde, Fundagão Oswaldo Cruz, Escola Nacional de Sakle PUblica 19:255-261 (2003).

Southworth, Exine development in *Gerbera jamesonii* (Asteraceae: Mutisieae), American Journal of Botany 70:1038-1047 (1983).

Carleton et al., Prevalence of *Dirofilaria immitis* and gastrointestinal helminths in cats euthanized at animal control agencies in northwest Georgia, Veterinary Parisitology 119:319-326 (2004).

Foreyt, W.J., Veterinary Parasitology Reference Manual, Fifth Edition, 2001, ISBN 0-8138-2419-2.

Roberts, L.S., et al., Foundations of Parasitology, Fifth Edition, 1996, Library of Congress Card Catalog No. 94-72939, ISBN 0-687-26071-S.

Coulaud, J.P., et al., Albendazole: a new single dose anthelmintic. Study in 1465 patients, Acta Tropica 41:87-90 (1984).

Voller, "The Enzyme Linked Immunosorbent Assay", *Diagnostic Horizon*, vol. 2, No. 1, pp. 1-7, Feb. 1978.

ROUNDWORM COPROANTIGEN DETECTION

CROSS-REFERENCE TO RELATED APPLICATIONS

This application is a continuation of U.S. Ser. No. 11/763,592, filed Jun. 15, 2007 (now U.S. Pat. No. 7,736,660).

BACKGROUND OF THE INVENTION

1. Field of the Invention

The present invention relates to compositions, devices, kits and methods for the detection of roundworm in animals. More particularly, the invention relates to compositions, devices, kits and methods for detecting the presence or absence of roundworm in a fecal sample. Even more particularly, the present invention relates to antibody compositions, devices, kits, and methods for detecting the presence or absence of roundworm antigen in a fecal sample that may also include one or more of hookworm, whipworm, and heartworm antigen.

2. Description of the Prior Art

Intestinal roundworm infection is common in animals and, if left untreated, can cause serious disease and even death. Although it is relatively easy to diagnosis a roundworm-infected animal as having a parasitic worm (helminth) infection of some type, it is significantly more difficult to identify roundworm, specifically, as the causative worm. This is a problem because roundworm infections are best treated when the infected animal's caregiver has knowledge that roundworm is the specific source of the infection. For example, such knowledge allows the caregiver to treat the animal with a drug that is optimally potent against roundworm, and therefore to avoid using a drug or drug cocktail that is generally effective against parasitic worm infections, but not optimally effective against roundworm.

Current methods for diagnosis of roundworm infections primarily involve microscopic examination of fecal samples, either directly in fecal smears or following concentration of ova and parasites by flotation in density media. Despite this procedure's high adoption, the method has significant shortcomings. These microscopic methods are time consuming, require specialized equipment and have low specificity. In addition, the accuracy of results of these methods is highly dependent upon the skill and expertise of the operator.

Taxonomic distinctions generally also may be made at a molecular level by determining whether one or more antigens of one or more antibodies to a particular worm species or to a defined group of worm species are present in an animal. For example, Hill et al. (*Veterinary Parasitology* (1997), vol. 68, pp. 91-102) disclose an enzyme-linked immunosorbent assay (ELISA) test for the detection of antibodies specific for whipworm in sera from porcine animals. While the test of Hill et al. does not crossreact with sera from pigs infected with roundworm or hookworm, it has not been determined, whether the test crossreacts with sera from pigs infected with heartworm. Similarly, Yamasaki et al. (*J. Clin. Microbiology* (2000), vol. 38, pp. 1409-1413) disclose an ELISA test utilizing a recombinant roundworm antigen for the detection of antibodies specific for roundworm in human sera. Whereas the assay of Yamasaki et al. has been shown to not be crossreactive with hookworm or heartworm, it has not been determined whether it crossreacts with whipworm. Bungiro and Cappello (*A. J. Trop. Med. Hyg.* (2005), vol. 73, pp. 915-920) disclose an ELISA to detect infection by the hookworm *Ancylostoma ceylanicum* in an experimental hamster model system but it has not been determined whether their test also crossreacts with one or more of roundworm, whipworm and heartworm.

Clinicians have shown little interest in using these assays to diagnose worm-infected animals. One reason why these assays have not been adopted is that researchers have not demonstrated that any of them are capable of specifically detecting a particular type of worm at the exclusion of all other major types of worms. For example, no one has yet developed an assay that specifically detects roundworm but that also has been shown to not crossreact with hookworm, whipworm and heartworm. This inability to pinpoint an animal's infection to a single source would cause uncertainty in diagnosis, and therefore would likely result in the administration of suboptimal treatment.

Further, some of these assays only have been shown to be useful for detecting antigens or antibodies in a serum sample. This is limiting because it often is impractical or difficult to obtain a serum sample from a sickened animal. For instance, in the case of an uncooperative animal, it may be difficult to stabilize the animal for the purpose of withdrawing blood, and in the case of a very sick animal, it may be impractical to transport the animal to a clinician's office for that same purpose. Testing for the presence or absence of a particular worm type therefore is better performed using an animal material that is readily obtainable and that does not require transportation of the animal, such as feces. Antigens present in fecal samples are referred to as coproantigens. In the case of the parasitic worm antigens that are subject of the present invention, coproantigens are worm antigens present in a fecal sample of a host animal.

Another limitation inherent to some of these assays is that they involve the production and purification of a specific recombinant antigen. Specifically, this is limiting because the steps required to produce and purify such an antigen can be costly and time-consuming.

What is needed therefore are compositions, devices, kits and methods for detecting the presence or absence of roundworm in a fecal sample. The needed compositions, devices, kits and methods further should be able to specifically detect the presence or absence of roundworm in a fecal sample that contains one or more of hookworm, whipworm, and heartworm.

SUMMARY OF THE INVENTION

The present invention is based in part on the discovery of an unexpected property of polyclonal antibodies. Specifically, it was determined that polyclonal antibody raised against either whole roundworm extract, roundworm reproductive tract extract, or roundworm intestinal tract extract, can be used to capture and detect the presence or absence of roundworm coproantigens in a mammal that is infested by one or more of whipworm, heartworm and hookworm. This specificity for roundworm is surprising since roundworms, whipworms, heartworms and hookworms all are related nematodes, and a polyclonal antibody raised against a whole extract, roundworm reproductive tract extract, or roundworm intestinal tract extract, of any one of these worms would be expected to crossreact with one or more of the other worms, host antigens, or other fecal components. The invention includes assay conditions under which the antibodies of the invention can be used to specifically capture and detect the presence or absence of roundworm coproantigens in a mammal that may also be infested by one or more of whipworm, heartworm and hookworm.

The invention, in one aspect, is a device for detecting the presence or absence of roundworm in a fecal sample in a mammal, such as a canine, feline, bovine, or human, for example. The invention further provides a device for detecting the presence or absence of roundworm in a fecal sample of a mammal that may also be infected with one or more of hookworm, whipworm, and heartworm. In one aspect of the invention, the device includes a solid support, wherein one or more polyclonal antibodies specific for one or more roundworm antigens are immobilized on the solid support.

In certain aspects of the invention, the device of the invention includes a lateral flow immunoassay device. In other aspects of the invention, the device of the invention includes an ELISA device.

The invention also includes antibodies and antibody compositions. More specifically, the invention relates to polyclonal antibodies that are capable of specifically binding roundworm coproantigen in a mammal that may also be infected with one or more of hookworm, whipworm or heartworm. The antibodies of the invention do not substantially bind hookworm, whipworm or heartworm antigen in a fecal sample. The present invention further includes methods of producing such antibodies.

The invention also is a method of detecting the presence or absence of roundworm in a fecal sample. The method includes contacting a fecal sample with the antibodies and capturing and detecting the presence or absence of roundworm coproantigens in that fecal sample. The detection step may include the detection of the presence or absence of an antigen/antibody complex. The method may further involve providing a second antibody that binds to the antigen of the antigen/antibody complex.

The invention further includes assay kits for detecting roundworm coproantigen in a fecal sample obtained from a mammal. A kit therefore may include one or more compositions and/or devices of the present invention. For example, the kit may include anti-roundworm antibodies and means for determining binding of the antibodies to roundworm antigens in the sample. In one particular example, such a kit includes the device having an immobilized anti-roundworm antibody, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, may be included in such test kits. A kit may further include instructions for carrying out one or more methods of the present invention, including instructions for using any device of the present invention that is included with the kit.

DETAILED DESCRIPTION OF THE PREFERRED EMBODIMENT

The present invention, in one aspect, is a device for the detection of intestinal roundworm infection in a mammal, such as a canine, feline, bovine, or human, for example. The device is arranged to aid in the detection of the presence or absence of roundworm coproantigen in a fecal sample from a mammal that may also be infected with one or more of hookworm, whipworm, and heartworm. In one aspect of the invention, the device includes a solid support, wherein one or more polyclonal antibodies, raised against whole roundworm extract, roundworm reproductive tract extract, and/or roundworm intestinal tract extract, and specific for one or more roundworm antigens, are immobilized on the solid support. The solid support can be, for example, a plate or a substrate in a lateral flow device.

Figure 1A:
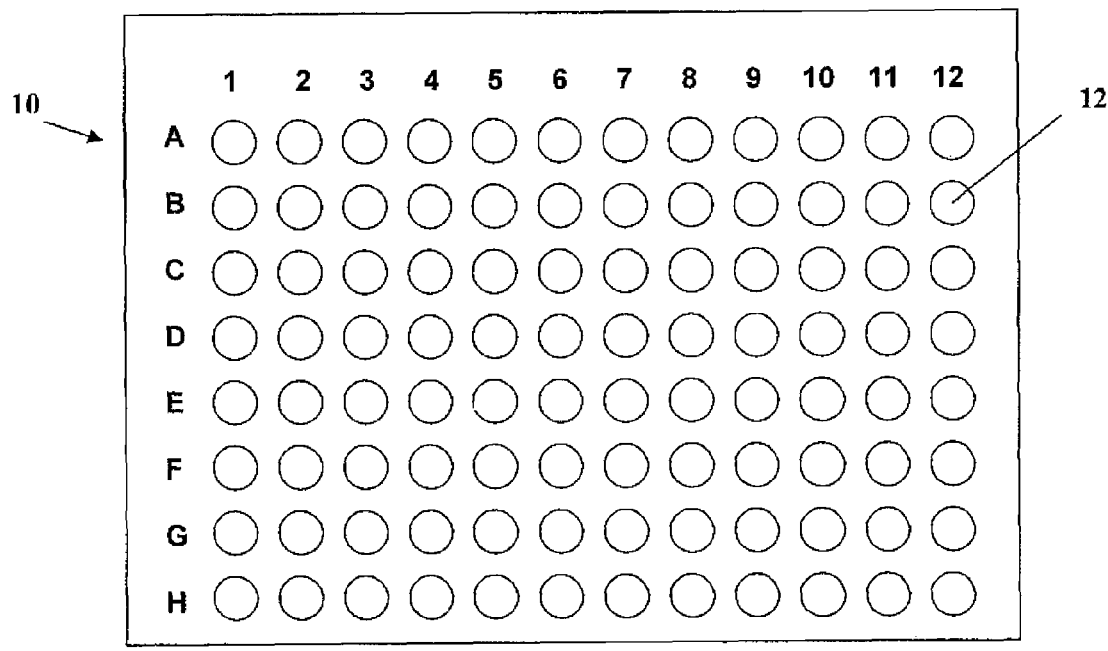
FIG. 1A shows a multi-well plate device of the present invention.
Figure 1B:
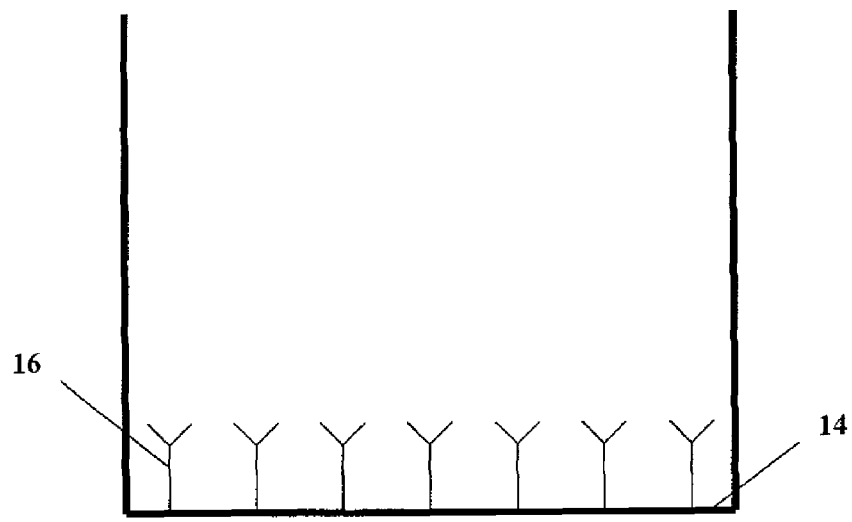
FIG. 1B shows a close up of a single well of the plate of FIG. 1A with an example representation of antibodies immobilized thereto.

As shown in FIGS. 1A and 1B, the device of the present invention is, for example, a multi-well plate 10 including a plurality of wells 12. Each well 12 provides a solid support 14 for immobilizing thereon a polyclonal antibody 16 specific to roundworm. The plate 10 may be an Immulon 1B 96-well plate, but is not limited thereto. Alternatively, the device could be a lateral flow assay such as that described in U.S. Pat. No. 5,726,010.

The polyclonal antibody 16, generally designated "anti-*Toxocara* pAB", that is immobilized on the solid support 14 is produced by administering a whole extract of a species of *Toxocara* or an extract of a portion, such as all or part of the reproductive tract or all or part of the intestinal tract, of a species of *Toxocara* to an animal, such as a rabbit, for example, collecting serum from that animal and purifying the anti-*Toxocara* pAB. Anti-*Toxocara* pAB specifically is immobilized onto the solid support 14 of the well 12 of the plate 10 by physical adsorption. Immobilization of anti-*Toxocara* pAB onto the solid support 14 is performed so that anti-*Toxocara* pAB will not be washed away by any procedures that may be performed, and so that the specific binding of antigens in a fecal sample to anti-*Toxocara* pAB is unimpeded by the solid support 14 or other device surface while the method of the present invention is being performed. The device 10 of the present invention is suitable for detecting roundworm antigen by the method of the present invention, which may include performing an ELISA assay.

The method of the invention may be used to detect one or more roundworm antigens in a sample. The test sample used in the method of the invention is a fecal sample. The method of invention may be used to test a fecal sample from any mammal, such as a feline, a canine, bovine or a human, for example.

The device 10 of the present invention, which includes anti-*Toxocara* pAB immobilized on the solid support 14, may be used in conjunction with a method of the present invention to detect roundworm in the fecal sample. Specifically, an active roundworm infection of an animal may be diagnosed by detecting one or more roundworm coproantigens with anti-*Toxocara* pAB that is immobilized on the solid support 14 of the device 10. "Roundworm coproantigens" are any roundworm components present in a fecal sample that can specifically and stably bind to anti-*Toxocara* pAB. Roundworm coproantigens therefore may be whole roundworm, roundworm eggs, roundworm fragments, products secreted, excreted or shed from roundworm or a combination thereof.

"Specific for" or "stably binds" means that anti-*Toxocara* pAB recognizes and binds to the roundworm coproantigen with greater affinity than to other coproantigens (e.g., a coproantigen from a non-roundworm parasitic worm). Binding specificity can be tested using methodology well known in the art, for example, ELISA or a radioimmunoassay (RIA). In a method of the present invention, roundworm antigen is detected by ELISA. A specific example of the ELISA method of the present invention follows. Although the present invention is described with respect to a specific ELISA method, however, it is to be understood that those of ordinary skill in the art will recognize that alternative, additional or substitute ELISA steps may be used without deviating from the basic goal.

A method of the present invention is specifically described with reference to two Examples, which together include five Experiments; however, it is not to be construed as being limited thereto.

Example A

The following materials and methods were used to generate data described in Experiments 1, 2, 3, and 4 described below.

Polyclonal antibody preparation. The polyclonal antibody "anti-*Toxocara* pAB" (IgG) was raised in rabbit against whole roundworm (*Toxocara canis*) extract (Antibody Systems Inc., Hurst, Tex.) and purified from serum by using standard methods. Briefly, an extract of disrupted whole roundworms was prepared by harvesting roundworms from infected canine animals, washing them, and resuspending them in solution. The resuspended worms were then disrupted by tissue homogenization, pelleted by centrifugation, and resuspended in solution. This resuspension was administered to rabbit and serum from the immunized rabbits was collected. Anti-*Toxocara* pAB was purified from the plasma of the immunized rabbits by isolating IgG antibody by protein G affinity chromatography.

Infection and anti-helminth treatment of canine and feline animals. For all four Experiments, parasitic nematode infection was effected by orally administering about 150-300 larvated eggs of either roundworm (*Toxocara*), hookworm (*Ancylostoma canium*), or whipworm (*Trichuris vulpis*) to a healthy canine or feline. (Specifically, *Toxocara canis* was the roundworm that was administered to canine and *Toxocara cati* was the roundworm that was administered to feline.) For Experiment 2, fecal samples were collected from canines known to be naturally infected with heartworm (*Dirofilaria immitis*). Further, for Experiments 3 and 4 only, canines were treated at post-infection day 91 and felines were treated at post-infection day 56 with Interceptor®, which is an anthelmintic agent commercially available from Novartis Animal Health Inc. of Basel, Switzerland, according to the manufacturer's protocol. It is well known by those of ordinary skill in the art that Interceptor® is effective for the removal of roundworms, hookworms, whipworms and heartworms from canine and feline animals. Infection was confirmed by microscopic observation of worm eggs in fecal samples obtained from these canine and feline animals. Canines and felines producing fecal samples that were found to be free of worm eggs by microscopic examination were considered to be uninfected.

Canine and feline fecal sample preparation. Canine and feline animals known to be free of parasitic worm infection or to be infected with one of either roundworm, hookworm, whipworm or heartworm provided the source of fecal samples. Samples (approximately 1 gram) from fresh, unpreserved canine or feline fecal samples were suspended in 4 ml of diluent solution ("diluent solution" is 0.05 M Tris base; 1 mM EDTA; 0.45% Kathon; 16 mg/ml gentamicin sulfate; 0.05% Tween-20; 40% fetal bovine serum; 10% rabbit serum; and 5% mouse serum). The suspension was centrifuged at 4000 rpm for 20 minutes to produce a first supernatant. The first supernatant was centrifuged at 12000 rpm for 5 minutes to produce a second supernatant, which is referred to herein as "fecal extract".

ELISA assays. Purified anti-*Toxocara* pAB (5 µg/ml; 100 µl/well) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 µl of fecal extract was added to each well and allowed to incubate at room temperature for one hour. The wells were washed five times with a PBS-Tween-20 solution according to standard methods known to those of ordinary skill in the art. Free anti-*Toxocara* pAB was labeled with horseradish peroxidase (HRP) by using the crosslinker succinimidyl 4-[N-maleimidomethyl]cyclohexane-1-carboxylate (SMCC) to create a conjugate, and 10 µg/ml of this conjugate was added to each well of the 96-well plate. Following a 30' incubation period at room temperature, unbound conjugate was washed from the wells using PBS-Tween-20 solution according to standard methods known to those of ordinary skill in the art. 50 µl TMBLUE® peroxidase substrate (SeraCare Life Sciences, West Bridgewater, Mass.) was then added to each well and the plates were incubated for 10' at room temperature. After stopping each enzymatic reaction with 0.1% sodium dodecyl sulfate (SDS) following the 10' incubation period, the optical density (OD) value of each well of the 96-well plate was measured at A650 by standard spectrophotometric techniques by using an ELISA plate reader. In this arrangement, the OD value obtained for any particular well of the 96-well plate was directly proportional to the amount of specifically bound antigen present in the well.

Experiment 1

Anti-*Toxocara* pAB specifically binds roundworm, but does not specifically bind hookworm or whipworm, in canine fecal samples.

Figure 2:
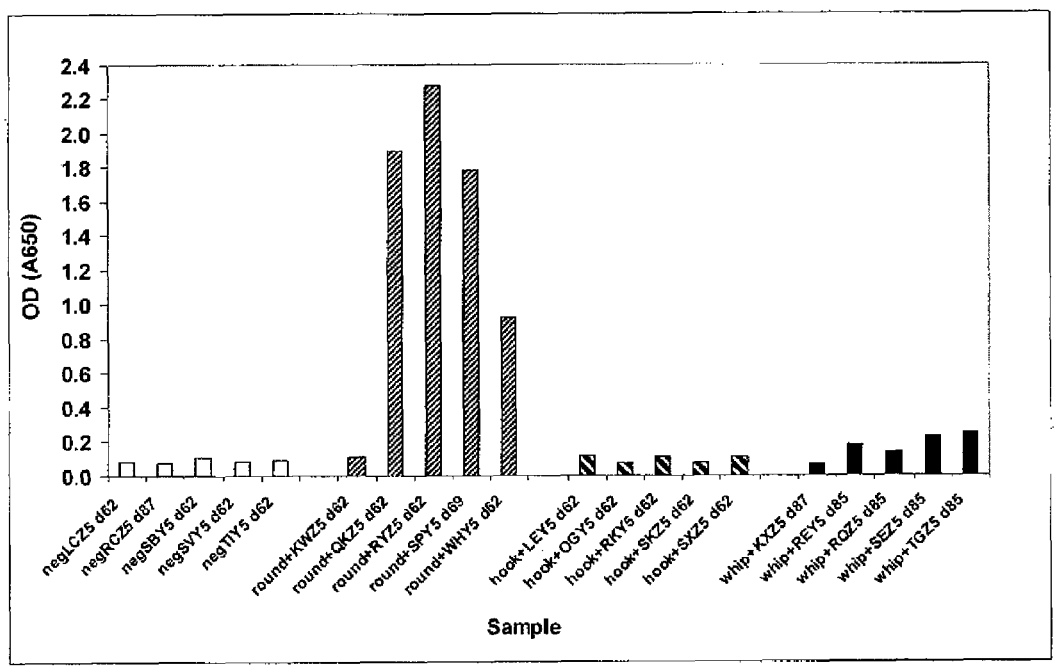
FIG. 2 shows a graph of optical density (OD) values obtained from canine fecal samples by following a method of the present invention in a first experiment.

It was a goal of Experiment 1 to determine whether anti-*Toxocara* pAB specifically binds coproantigen of roundworm, hookworm, and/or whipworm in canines. OD determinations for 20 canine fecal samples obtained in Experiment 1 are shown in FIG. 2. Specifically, these fecal samples were obtained from five canine animals known to be free of parasitic worm infection (negLCZ5 d62, negRCZ5 d87, negSBY5 d62, negSVY5 d62, and negTIY5 d62), five canine animals known to be infected with roundworm (round+KWZ5 d62, round+QKZ5 d62, round+RYZ d62, round+SPY5 d69, and round+WHY5 d62), five canine animals known to be infected with hookworm (hook+LEY5 d62, hook+OGY5 d62, hook+RKY5 d62, hook+SKZ5 d62, and hook+SXZ5 d62), and five canine animals known to be infected with whipworm (whip+KXZ5 d87, whip+REY5 d85, whip+RQZ5 d85, whip+SEZ d85, and whip+TGZ d85). Fecal samples were obtained on either post-infection day 62 ("d62"), day 69 ("d69"), day 85 ("d85"), or day 87 ("d87"). The specific post-infection day chosen for each particular canine animal was based on the day that worm egg output was at or near peak levels as determined by microscopic inspection.

The average OD measured of the uninfected, hookworm-infected, and whipworm-infected samples were 0.091, 0.099, and 0.172, respectively (the measured OD of each one of these samples was <0.25), indicating that anti-*Toxocara* pAB did not specifically bind antigen in any of these samples. Conversely, the average OD of the fecal samples from roundworm-infected canines was 1.40, which was about eight times higher than obtained for the whipworm-infected samples, and about 15 times higher than obtained for both the uninfected and hookworm-infected samples. These data indicate that anti-*Toxocara* pAB specifically binds one or more roundworm antigens, but does not specifically bind any hookworm or whipworm coproantigen.

Experiment 2

Anti-*Toxocara* pAB does not specifically bind heartworm in canine fecal samples.

Figure 3:
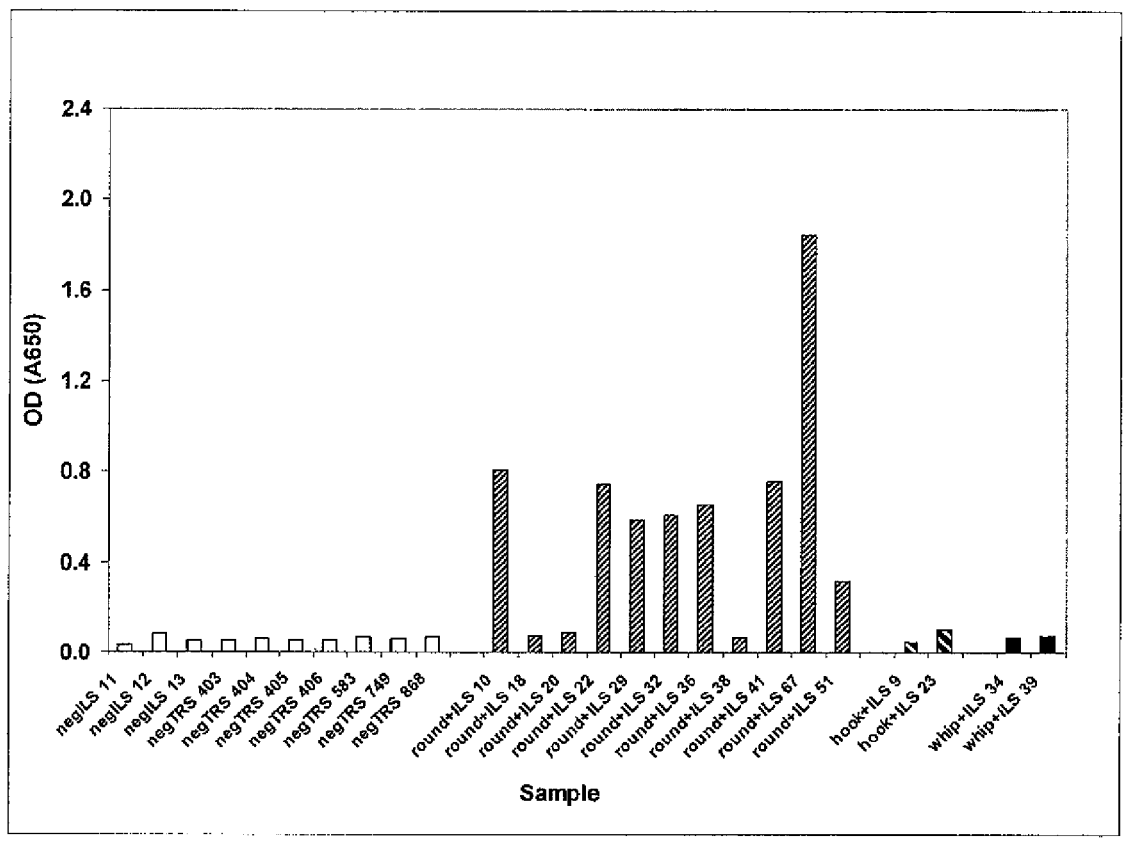
FIG. 3 shows a graph of OD values obtained from canine fecal samples by following the method of the present invention in a second experiment.

It was a goal of Experiment 2 to determine whether anti-*Toxocara* pAB specifically binds heartworm coproantigen. OD determinations for 25 canine fecal samples obtained in a second experiment are shown in FIG. 3. Specifically, FIG. 3 shows data obtained as the result of testing fecal samples from three canine animals known to be free of parasitic worm infection (negILS 11, negILS 12, and negILS 13), seven canine animals known to be naturally infected with heartworm (negTRS 403, negTRS 404, negTRS 405, negTRS 406, negTRS 583, negTRS 749, and negTRS 868), 11 canine animals know to be infected with roundworm (round+ILS 10, round+ILS 18, round+ILS 20, round+ILS 22, round+ILS 29, round+ILS 32, round+ILS 36, round+ILS 38, round+ILS 41, round+ILS 67, and round+ILS 51), two canine animals known to be infected with hookworm (hook+ILS 9 and hook+ILS 23), and two canine animals known to be infected with whipworm (whip+ILS 34 and whip+ILS 39).

The average OD of the uninfected, heartworm-infected, hookworm-infected, and whipworm-infected samples were 0.058, 0.061, 0.074, and 0.074, respectively (the measured OD of each one of these samples was 0.101 or less), indicating that anti-*Toxocara* pAB did not specifically bind antigen in any of these samples. Conversely, the average OD of the fecal samples from roundworm-infected canines was 0.599, which was about 10 times higher than the average OD measured in the uninfected and heartworm-infected samples, and about eight times higher than the average OD of the whipworm-infected samples and the hookworm-infected samples. In addition to providing further confirmation that anti-*Toxocara* pAB specifically binds one or more roundworm antigens, but does not specifically bind any hookworm or whipworm coproantigen, this second experiment demonstrates that anti-*Toxocara* pAB does not specifically bind any heartworm coproantigen.

Experiment 3

Anti-*Toxocara* pAB detects roundworm in feces from a canine animal only when the animal has an active roundworm infection.

Once it was determined that anti-Toxocara pAB specifically binds roundworm, but not hookworm, whipworm or heartworm, Experiment 3 was performed to determine whether anti-Toxocara pAB detects roundworm only at appropriate times (that is, only when the host animal has an active roundworm infection). Toward this goal, ELISA data was obtained from all of the uninfected canines and roundworm-infected canines described in Experiments 1 and 2. Specifically, data was generated from fecal samples obtained from all or some of these roundworm-infected animals one day prior to infection ("−1"), and at days 23, 31, 38, 44, 48, 52, 93, and 105 post-infection. Microscopic inspection of these fecal samples indicated that the samples obtained on days 38, 44, 48, 52, and 93, but not on days −1, 23, 31, and 105, were substantially infected with roundworm eggs. (The absence of a substantial number of roundworm eggs on days 23 and 31 is consistent with the roundworm life cycle in canines. That is, it is well known in the art that orally administered worm eggs do not manifest in canine fecal material in substantial numbers until about one month after introduction. Further, it is expected that the absence of a substantial number of roundworm eggs on day 105 was due to the anthelmintic treatment administered on day 91.)

Figure 4:
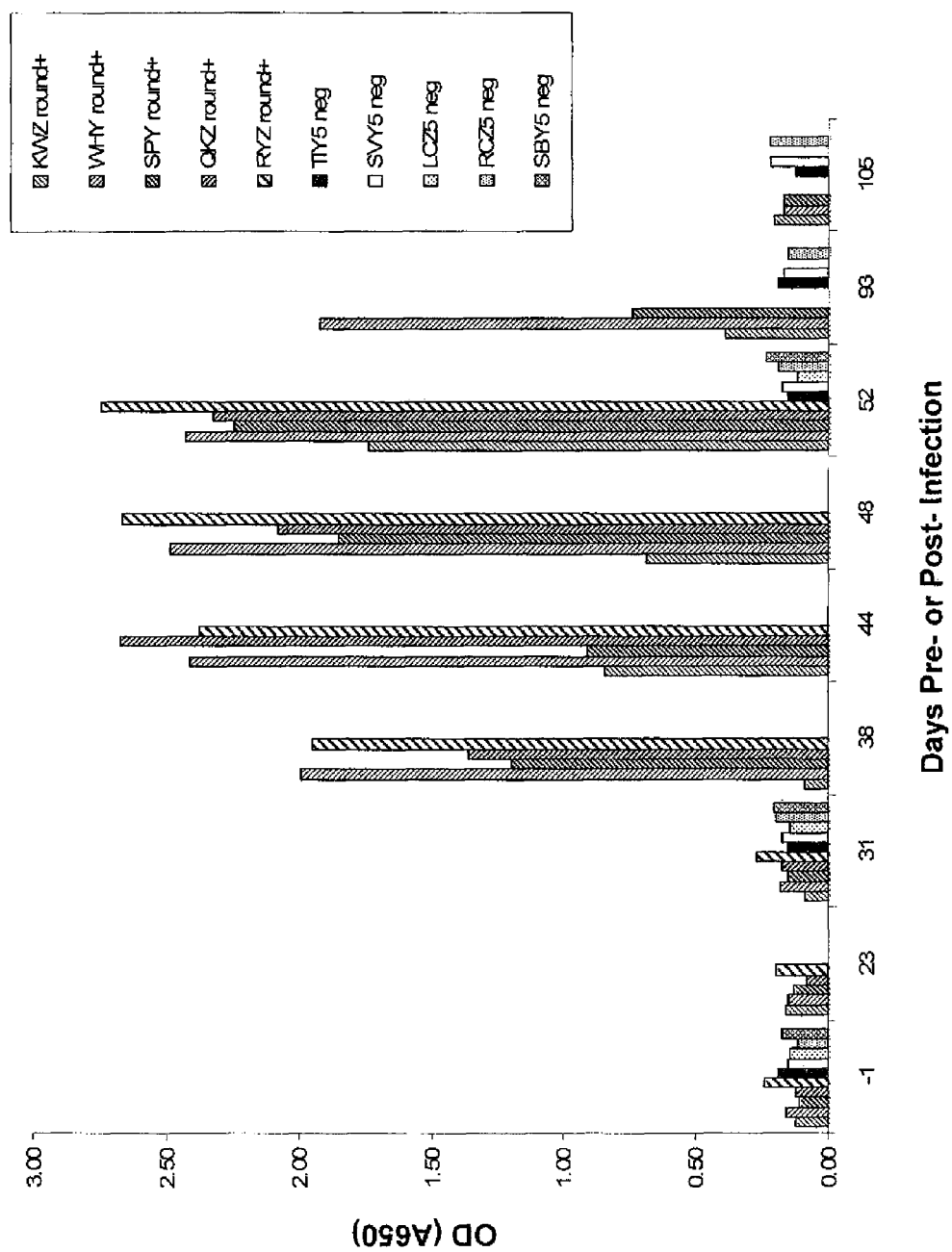
FIG. 4 shows a graph of OD values obtained from canine fecal samples by following the method of the present invention in a third experiment.

As shown in FIG. 4, roundworm was detected by the method of the present invention only in fecal samples that were microscopically determined to be substantially infected with roundworm eggs (i.e., only in samples obtained on days 38, 44, 48, 52, and 93). Specifically, the average OD value generated from fecal samples from roundworm-infected canines on each of days −1, 23, 31, and 105 (which were microscopically determined to be substantially free of roundworm eggs), was <0.180. The average OD value generated from fecal samples from roundworm-infected canines on each of days 38, 44, 48, 52, and 93 was 1.316, 1.842, 1.896, 2.295, 1.104, which represents a range of about a six-fold to about a 12-fold increase in OD over the egg-free samples.

Experiment 3 therefore indicates that anti-*Toxocara* pAB specifically binds roundworm coproantigen only when a host animal has an active roundworm infection.

Experiment 4

Anti-*Toxocara* pAB specifically binds roundworm coproantigen in a feline fecal sample, and does so only when the feline from which the sample was obtained has an active roundworm infection.

It was a goal of Experiment 4 to determine whether anti-*Toxocara* pAB specifically binds coproantigen of roundworm in felines.

Figure 5:
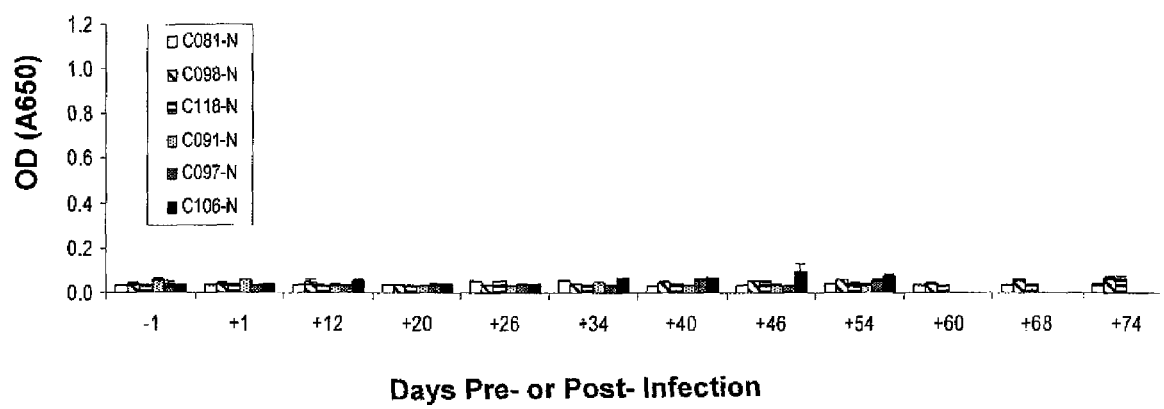
FIG. 5 shows a first graph of OD values obtained from feline fecal samples by following the method of the present invention in a fourth experiment.
Figure 6:
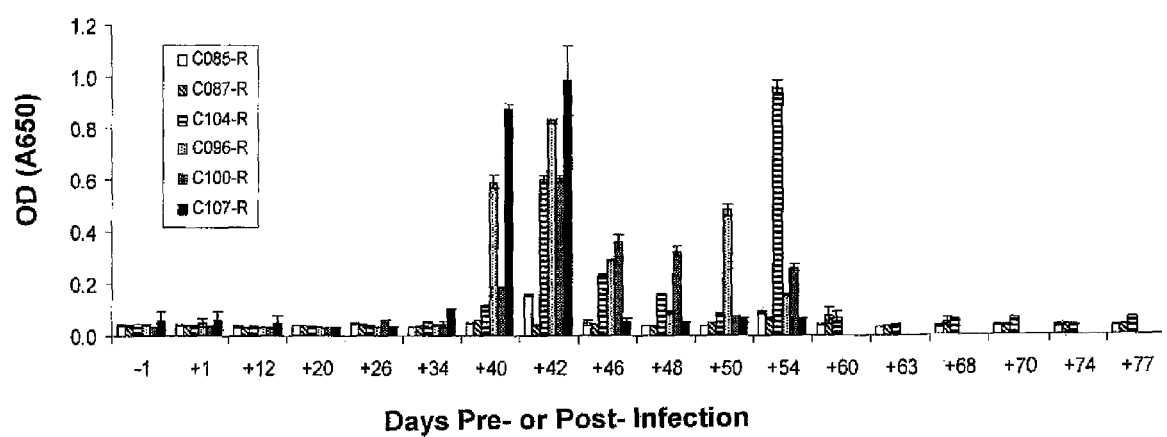
FIG. 6 shows a second graph of OD values obtained from feline fecal samples by following the method of the present invention in the fourth experiment.

OD values measured for fecal samples obtained from uninfected felines and roundworm-infected felines are shown in FIGS. 5 and 6, respectively. Specifically, FIG. 5 shows average OD values (and standard deviations) measured using fecal samples from uninfected felines over the course of 75 days. (Each OD value shown in FIG. 5 is the average of six OD values obtained from the same fecal sample in six separate ELISA reactions.) Data from the same six uninfected felines, which are designated C081-N, C098-N, C118-N, C091-N, C097-N, and C106-N, are shown for days −1 (i.e., one day before administration of hookworm infection to the hookworm-infected animals) and 54, and for selected days therebetween. Further, data from three of these six felines, C081-N, C098-N and C118-N, also are shown for each of days 60, 68 and 74.

FIG. 6 shows average OD values (and standard deviations) generated using fecal samples taken from hookworm-infected felines over the course of 78 days. (Each OD value shown in FIG. 6 is the average of six OD values generated from the same fecal sample in six separate ELISA reactions.) Data from the same six feline animals, which are designated C085-R, C087-R, C104-R, C096-R, C100-R and C107-R, are shown for days −1 (i.e., one day before administration of roundworm infection to the animals) and 54, and for selected days therebetween. Further, data from three of these six felines, C085-R, C087-R and C104-R, are shown for days 60 and 77, and for selected days therebetween.

Referring to FIG. 5, the average of the average OD values measured for the uninfected felines was 0.059 or less for each of days −1 and 74 and the selected days therebetween. Referring to FIG. 6, the average of the average OD values measured for the roundworm-infected felines was 0.053 or less for each of days −1 and 34 and the selected days therebetween. On day 40, the average of the average OD values measured for the roundworm-infected felines was 0.312, which is about 10-fold higher than was seen in the uninfected felines for each of days −1 and 74 and the selected days therebetween, and in the roundworm-infected felines at days −1 and 34 and the selected days therebetween. Further, several average OD values measured for some of the roundworm-infected felines on post-infection days 42, 46, 48, 50 and 54 were several-fold higher than was seen in the uninfected felines for each of days −1 and 74 and the selected days therebetween, and in the roundworm-infected felines at days −1 and 34 and the selected days therebetween.

These data indicate that anti-*Toxocara* pAB specifically binds one or more coproantigen of roundworm. These data further indicate that anti-*Toxocara* pAB may be used to determine whether a feline is or is not infected with roundworm.

It was another goal of Experiment 4 to determine whether anti-*Toxocara* pAB detects roundworm only when a feline animal has an active roundworm infection.

Microscopic observation of the fecal samples taken from the roundworm-infected canine animals on post-infection day 60 showed that the samples were moderately free of roundworm ova, and microscopic observation of the fecal samples taken from the hookworm-infected animals on post-infection days 63, 68, 70, 74 and 77 showed that the samples were substantially free of roundworm ova. It is expected that the moderate reduction in ova on post-infection day 60 and the substantial reduction in ova on post-infection days 63, 68, 70, 74 and 77 was due to the anthelmintic treatment administered on post-infection day 56. Referring to FIG. 6, the average of the average OD values measured for the roundworm-infected felines was consistent with the observed reduction of ova number in the fecal samples taken from these animals. Specifically, the average of the average OD value measured for these canines on the days following anthelmintic treatment was 0.063 (day 60) or less.

These data indicate that anti-*Toxocara* pAB specifically binds one or more coproantigen of roundworm. These data further indicate that anti-*Toxocara* pAB may be used to determine whether a feline has or does not have an active roundworm infection.

Example B

The following materials and methods were used to generate data described in Experiment 5 described below.

Polyclonal antibody preparation. One preparation of anti-*Toxocara* pAB (IgG) was raised in rabbits against extracts from roundworm (*T. canis*) intestine and a second preparation of anti-*Toxocara* pAB (IgG) was raised in rabbits against extracts from roundworm (*T. canis*) reproductive organs, and both preparations were purified from serum by using standard methods. (For clarity, anti-*Toxocara* pAB raised against intestine is more specifically referred to as being "anti-TGUT pAB" and anti-*Toxocara* pAB raised against reproductive organs is more specifically referred to as being "anti-TOVA pAB".) Briefly, extracts from dissected female roundworm intestine or male and female reproductive organs were prepared by harvesting roundworms from infected canine animals, washing them, and dissecting the organs. The organs were ground in liquid nitrogen and suspended in Hanks Balanced Salt solution having protease inhibitor. This suspension was administered to rabbits and serum from the immunized rabbits was collected. Anti-TGUT pAB and anti-TOVA pAB were purified from the plasma of the immunized rabbits by isolating IgG antibody by protein G affinity chromatography.

Infection and anti-helminth treatment of canine animals. For Experiment 5, parasitic nematode infection was effected by orally administering about 150-300 larvated eggs of either roundworm (*T. canis*), hookworm, or whipworm to a healthy canine. Infection was confirmed by microscopic observation of worm eggs in fecal samples obtained from these canine animals. Canines producing fecal samples that were found to be free of worm eggs by microscopic examination were considered to be uninfected.

ELISA assays. Purified anti-TGUT pAB or anti-TOVA pAB (3-9 µg/ml; 100 µl/well) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 µl of fecal extract (prepared as described above) was added to each well and allowed to incubate at room temperature for one hour. The wells were washed five times with a PBS-Tween-20 solution according to standard methods known to those of ordinary skill in the art. Free anti-TGUT pAB or anti-TOVA pAB was labeled with HRP by using SMCC to create a conjugate, and 3-9 µg/ml of this conjugate was added to each well of the 96-well plate. Following a 30' incubation period at room temperature, unbound conjugate was washed from the wells using PBS-Tween-20 solution according to standard methods known to those of ordinary skill in the art. 50 µl TMBLUE® peroxidase substrate (SeraCare Life Sciences, West Bridgewater, Mass.) was then added to each well and the plates were incubated for 10' at room temperature. After stopping each enzymatic reaction with 0.1% SDS following the 10' incubation period, the OD value of each well of the 96-well plate was measured at A650 by standard spectrophotometric techniques by using an ELISA plate reader. In this arrangement, the OD value obtained for any particular well of the 96-well plate was directly proportional to the amount of specifically bound antigen present in the well.

Experiment 5

Each of anti-TGUT pAB and anti-TOVA pAB specifically bind roundworm, but neither specifically binds hookworm or whipworm, in canine fecal samples.

Figure 7:
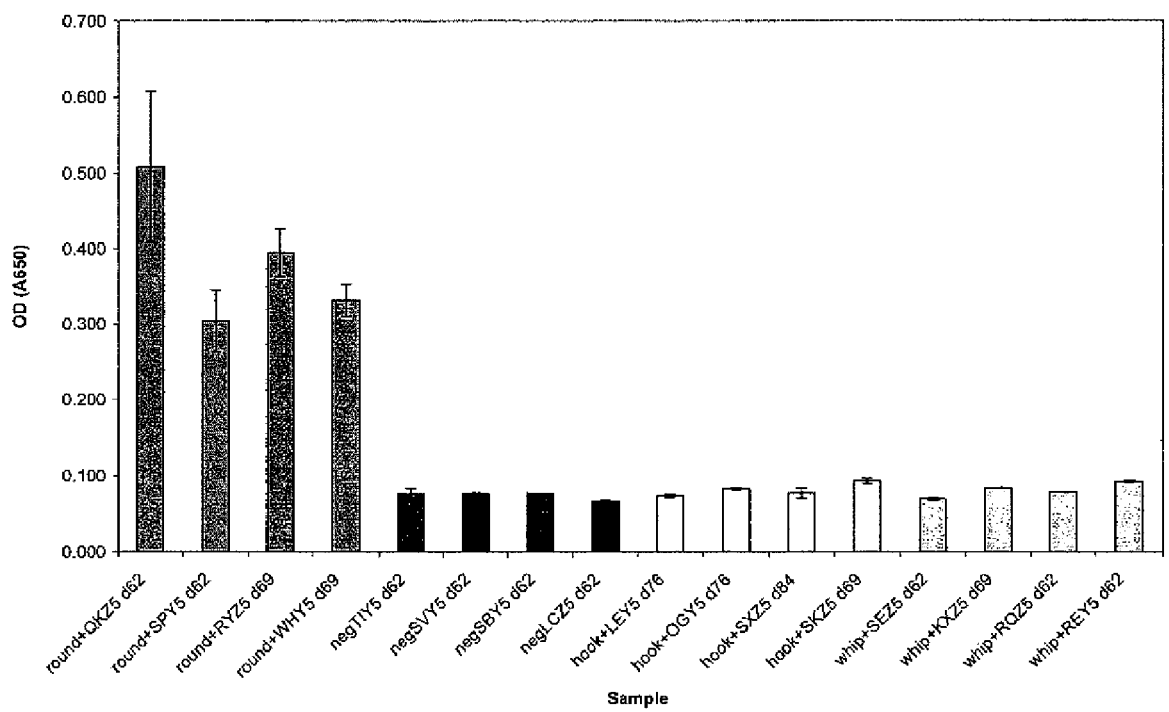
FIG. 7 shows a first graph of OD values obtained from canine fecal samples by following the method of the present invention in a fifth experiment.
Figure 8:
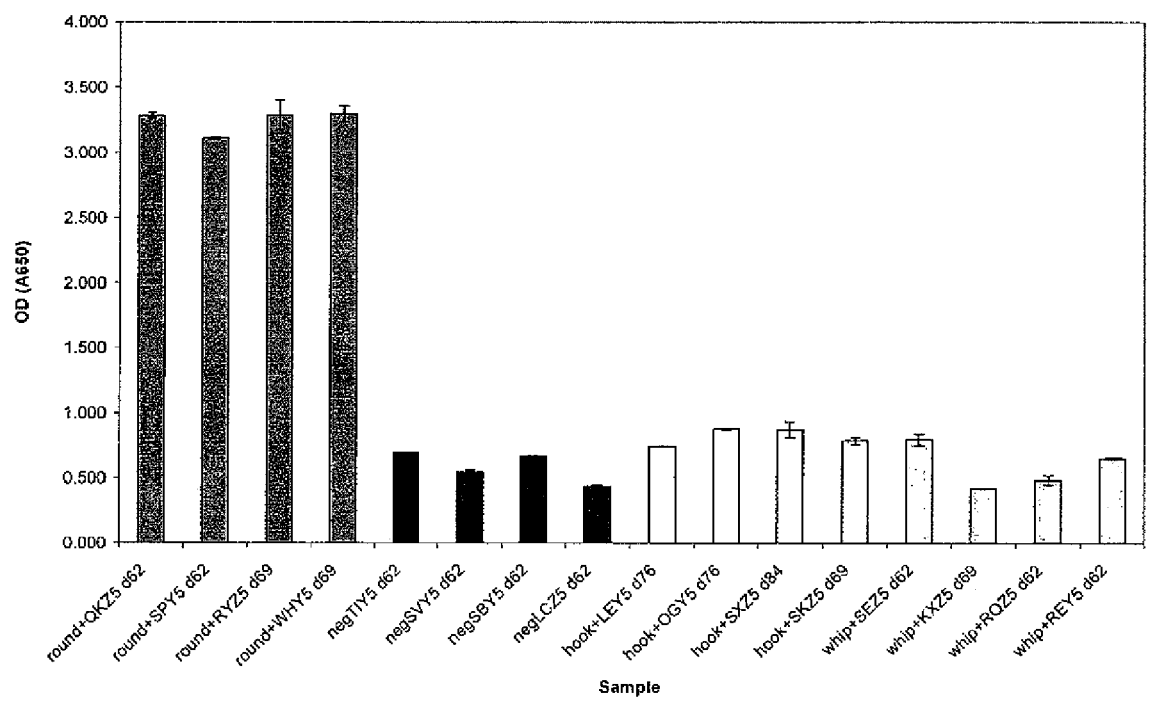
FIG. 8 shows a second graph of OD values obtained from canine fecal samples by following the method of the present invention in the fifth experiment.

It was a goal of Experiment 5 to determine whether antibody raised against roundworm intestinal tract, specifically referred to as "anti-TGUT pAB", and/or antibody raised against roundworm reproductive tract, specifically referred to as "anti-TOVA pAB", specifically binds coproantigen of roundworm, hookworm, and/or whipworm. OD determinations for 16 canine fecal samples obtained in Experiment 5 are shown in each of FIGS. 7 and 8. (FIG. 7 shows OD values obtained using anti-TGUT pAB and FIG. 8 shows OD values obtained using anti-TOVA pAB.) Specifically, these fecal samples were obtained from four canine animals known to be free of parasitic worm infection (negTIY5 d62, negSVY5 d62, negSBY5 d62, and negLCZ5 d62), four canine animals known to be infected with roundworm (round+QKZ5 d62, round+SPY5 d62, round+RYZ d69, and round+WHY5 d69), four canine animals known to be infected with hookworm (hook+LEY5 d76, hook+OGY5 d76, hook+SXZ5 d84, and hook+SKZ5 d69), and four canine animals known to be infected with whipworm (whip+SEZ d62, whip+KXZ5 d69, whip+RQZ5 d62, and whip+REY5 d62). Fecal samples were obtained on either post-infection day 62 ("d62"), day 69 ("d69"), day 76 ("d76"), or day 84 ("d84"). The specific post-infection day chosen for each particular canine animal was based on the day that worm egg output was at or near peak levels as determined by microscopic inspection.

Referring specifically to FIG. 7, for anti-TOUT pAB, the average OD measured of the uninfected, hookworm-infected, and whipworm-infected samples were 0.075, 0.083, and 0.082, respectively (the measured OD of each one of these samples was <0.096), indicating that anti-TGUT pAB did not specifically bind antigen in any of these samples. Conversely, the average OD of the fecal samples from roundworm-infected canines was 0.385, which was about 4.5 to 5 times higher than obtained for the uninfected, hookworm-infected and whipworm-infected samples. These data indicate that anti-TGUT pAB specifically binds one or more roundworm antigens, but does not specifically bind any hookworm or whipworm coproantigen.

Referring specifically to FIG. 8, for anti-TOVA pAB, the average OD measured of the uninfected, hookworm-infected, and whipworm-infected samples were 0.588, 0.820, and 0.590, respectively (the measured OD of each one of these samples was <0.916). Conversely, the average OD of the fecal samples from roundworm-infected canines was 3.244, which was about 4 to 5.5 times higher than obtained for the uninfected, hookworm-infected and whipworm-infected samples. These data indicate that anti-TGUT pAB specifically binds one or more roundworm antigens, but does not specifically bind any hookworm or whipworm coproantigen.

While the composition, device and method of the present invention have been described with respect to a specific embodiment and specific Examples, it is to be understood that variations to the device and/or the method of the present invention may be made without departing from the spirit and scope of the invention. For example, it is to be understood that a polyclonal antibody other than anti-*Toxocara* pAB, or monoclonal antibodies, single chain antibodies (scFv), chimeric antibodies, or fragments of an antibody may be substituted for anti-*Toxocara* pAB. Another polyclonal antibody that is specific for roundworm could be prepared, for example, by administering one or more antigens specific for roundworm to an animal. Further, whereas anti-*Toxocara* pAB was raised in rabbit, polyclonal antibody also may be raised in, for example, a human or other primate, mouse, rat, guinea pig, goat, pig, cow, sheep, donkey, dog, cat, chicken, or horse. An antibody used in the device of the invention also may be any antibody class, including for example, IgG, IgM, IgA, IgD and IgE. Means for preparing and characterizing antibodies are well know in the art. See, e.g., Dean, *Methods Mol. Biol.* 80:23-37 (1998); Dean, *Methods Mal. Biol.* 32:361-79 (1994); Bailegi, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992).

An antibody used in the devices, methods and kits of the invention can also be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F, fragments.

Antibodies used in the device of the invention may be immobilized on the solid support by any methodology known in the art, including, for example, covalently or non-covalently, directly or indirectly, attaching the antibodies to the solid support. Therefore, while anti-*Toxocara* pAB is attached to the solid support by physical adsorption (i.e., without the use of chemical linkers) in the embodiment described, it is contemplated that anti-*Toxocara* pAB or other antibodies may be immobilized to the solid support by any chemical binding (i.e., with the use of chemical linkers) method readily known to one of skill in the art.

The solid support of the device is not limited to being a polystyrene 96-well plate. The solid support may be any suitable material for the immobilization of antibodies specific for roundworm. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, dextran, nylon, amylases, plastics, magnetite or any other suitable material readily known to one of skill in the art.

The device of the present invention also is not limited to being a device that is suitable for performing an ELISA assay. For example, the device may be one that is suitable for performing a lateral flow assay. An exemplary device that is useful for performing a lateral flow assay that is useful in the present invention is described in U.S. Pat. No. 5,726,010, which is incorporated herein by reference in its entirety. The device for performing a lateral flow assay therefore may be a SNAP® device, which is commercially available from IDEXX Laboratories, Inc. of Westbrook, Me.

The device may optionally include one or more labeled antigen capture reagents that may be mixed with a fecal sample prior to application to a device of the invention. When the labeled antigen reagent is included, the labeled antigen capture reagent may or may not be deposited or dried on the solid surface of the device. By "antigen capture" is meant any compound that is specific for the antigen of interest. The labeled antigen capture reagent, whether added to a fecal sample or pre-deposited on the device, may be, for example, a labeled antibody specific for a roundworm antigen. For example, a roundworm-specific antibody conjugated with horseradish peroxidase may be used as a labeled antigen capture reagent.

The device also may optionally include a liquid reagent that transports, such as when the device includes the SNAP® device, for example, or facilitates removal of, such as when the device includes a 96-well plate, for example, unbound material (e.g., unreacted fecal sample and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the detector reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess, unbound material is transported away from the second region, at which time detectable end product is produced.

The device of the present invention may also include various binding reagents immobilized at locations distinct from the antigen capture reagent(s). For example, an immunoreagent (an antibody, antigen or peptide) that recognizes a species-specific (e.g., worm-specific) antibody portion of a labeled antibody or antigen capture reagent or an enzyme portion of an enzyme-labeled reagent can be included as a positive control to assess the viability of the reagents within the device. For example, a positive control may be an anti-horseradish peroxidase antibody that has been raised in, for example, a goat or a mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to detect roundworm in a fecal sample, the device of the invention optionally may be designed to allow one or more other diagnostic tests to be performed. For example, the solid support may also include reagents for the detection of one or more non-roundworm worm parasites, one or more non-worm parasites, one or more viruses, or one or more bacteria. The reagents for the detection of one or more non-roundworm worm parasites, one or more non-worm parasites, one or more viruses or one or more bacteria may be, for example, one or more antibodies or one or more antigens recognized by antibodies specific for one or more non-roundworm worm parasites, one or more non-worm parasites, one or more viruses or one or more bacteria.

In the methods of the present invention, detection of a roundworm infection is accomplished by detecting the presence or absence of one or more roundworm antigens in a fecal sample. The soluble portion of a fecal sample to be tested may be collected by any protocol known in art. For example, in addition to the specific protocol described above, the soluble portions of the sample may be collected using filtration, centrifugation, or simple mixing followed by gravimetric settling.

The methods include contacting the fecal sample with one or more antibodies specific for one or more roundworm antigens under conditions that allow an antigen/antibody complex, i.e., an immunocomplex, to form. That is, an antibody specifically binds to a roundworm antigen present in the fecal sample. One of skill in the art would be familiar with assays and conditions that are used to detect antigen/antibody complex binding. For example, the antigen/antibody complex may be detected using a secondary antibody that binds to the antigen/antibody complex. The formation of a complex between roundworm antigen and anti-roundworm antibodies in the sample may be detected using any suitable method known in the art. Further, the amount of antibody-antigen complexes can be determined by methodology known in the art. A level that is higher than that formed in a control sample indicates a roundworm infection.

Alternative steps of the method of the present invention may include applying the fecal sample to a device of the invention, which includes an immobilized antibody specific for roundworm antigen, and detecting the presence or absence of the roundworm antigen in the fecal sample. Antibodies specific for antigens of roundworms may be directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

The method of the present invention need not include the use of solid phases or substrates, however. For example, the methods may include immunoprecipitation methods which do not require the use of solid phases or substrates.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by radiometric, calorimetric, fluorometric, size-separation, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody specific for a roundworm antigen.

Methods of the invention include, but are not limited to those based on competition, direct reaction or sandwich-type assays, including, but not limited to ELISA, RIA, immunofluorescent assays (IFA), hemagglutination (HA), fluorescence polarization immunoassay (FPIA), and microtiter plate assays (any assay done in one or more wells of a microtiter plate). One assay of the invention includes a reversible flow chromatographic binding assay, which may be performed, for example, by using a SNAP® device. See U.S. Pat. No. 5,726, 010.

Methods of the invention facilitate sandwich or competition-type specific binding assays. In a sandwich assay, antigen capture reagents are immobilized in a reactive zone. These antigen capture reagents may specifically bind to antigens in the fecal sample being tested. Specifically, these antigen capture reagents specifically bind to an antigen from a roundworm, if present in the fecal sample. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the invention, antibodies specific for a roundworm antigen or antigens are attached to a solid phase or substrate. The fecal sample potentially including an antigen from roundworm is added to the substrate. Antibodies that specifically bind roundworm are added. The antibodies may be the same antibodies used on the solid phase or they may be from a different source or species. Further, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer.

In other embodiments of the invention, antibodies specific for a roundworm antigen or antigens are attached to a solid phase or substrate. A fecal sample potentially including a roundworm antigen is added to the substrate. Second antispecies antibodies that specifically bind antigens of roundworms are added. These second antibodies are from a different species than are the solid phase antibodies. Third antispecies antibodies that specifically bind the second antibodies and that do not specifically bind the solid phase antibodies are added. The third antibodies may include an indicator reagent, such as an enzyme conjugate. Wash steps may be performed prior to each addition. A chromophore or enzyme substrate may added and color may be allowed to develop. The color reaction may be stopped and the color may be quantified using, for example, a spectrophotometer.

In a specific example, the method of the present invention is performed in conjunction with a device that is a lateral flow assay device by adding a prepared fecal sample to a flow matrix of the device at a first region (a sample application zone). The prepared fecal sample is carried in a fluid flow path by capillary action to a second region of the flow matrix where a particulate label capable of binding and forming a first complex with an antigen in the fecal sample. The particulate label can be, e.g., a colored latex particle, dye sol, or gold sol conjugated to an antibody specific for a roundworm antigen. The first complex is carried to a third region of the flow matrix where an antibody that specifically binds a roundworm antigen is immobilized at a distinct location. A second complex is formed between the immobilized antibody and the first complex. The particulate label that is part of the second complex can be directly visualized.

Roundworm antibody may be an immobilized antigen capture reagent in a reaction zone (solid phase). A second antigen capture reagent, i.e., a second roundworm antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

The invention further includes assay kits (e.g., articles of manufacture) for detecting roundworm in a fecal sample. A kit therefore may include one or more devices of the present invention. For example, the kit may include anti-roundworm antibodies and means for determining binding of the antibodies to roundworm antigens in the sample. In one particular example, such a kit includes the device having an immobilized anti-roundworm antibody, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The antibodies, assays, and kits of the invention are useful, for example, in the diagnosis of individual cases of roundworm infection in a patient, as well as epidemiological studies of roundworm outbreaks. The kit may further include instructions for carrying out one or more methods of the present invention, including instructions for using any device of the present invention that is included with the kit.

The methods of the invention for detection of roundworm infection can be combined with other diagnostic assays to detect the presence of other organisms or conditions. For example, assays of the invention can be combined with reagents that detect one or more non-roundworm worm fecal parasite, one or more non-worm fecal parasite, one or more virus, one or more bacteria, one or more blood-borne parasites or occult blood or a combination thereof. By providing two or more unique binding sites in a single assay device (such as, for example, two unique spots on a SNAP® assay device), the present invention allows for detection of two or more organisms from a single sample. In one embodiment, there are three unique spots for detection of past or present infection from three organisms (the spots being either antigen or antibody binding reagents) from a single sample (i.e. the same, single sample is presented to the three capture reagents on a single device).

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

A number of examples to help illustrate the invention have been described. Nevertheless, it will be understood that various modifications may be made without departing from the spirit and scope of the invention. Accordingly, other embodiments are within the scope of the claims appended hereto.

What is claimed is:

1. A device for detecting the presence or absence of *Toxocara* roundworm antigen in a fecal preparation from a mammal, comprising a solid support, wherein one or more antibodies specific for one or more *Toxocara* roundworm antigens are immobilized on the solid support.

2. The device of claim 1 wherein the one or more antibodies specific for one or more *Toxocara* roundworm antigens are not specific for any coproantigen present in the fecal preparation selected from the group consisting of hookworm, whipworm, and heartworm.

3. The device of claim 1 wherein the one or more antibodies are specific for an extract of whole *Toxocara* roundworm, an extract of *Toxocara* roundworm intestine or an extract of *Toxocara* roundworm reproductive organ.

4. The device of claim 3 wherein the *Toxocara* roundworm is *Toxocara canis*.

5. The device of claim 1 wherein one or more of the one or more antibodies are specifically bound to one or more *Toxocara* roundworm coproantigens.

6. The device of claim 1 wherein one or more of the one or more antibodies are labeled.

7. The device of claim 1 wherein the device is an enzyme-linked immunosorbent assay device.

8. The device of claim 7 wherein the enzyme-linked immunosorbent assay device is a lateral flow immunoassay device.

9. The device of claim 1 wherein the mammal is a canine or a feline.

10. The device of claim 1 wherein the device further includes one or more reagents for the detection of one or more of the group consisting of: one or more non-roundworm worm parasites, one or more non-worm parasites, one or more viruses, and one or more bacteria, said one or more reagents selected from the group consisting of one or more antibodies or one or more antigens recognized by antibodies specific for one or more non-roundworm parasites, one or more non-worm parasites, one or more viruses and one or more bacteria.

11. The device of claim 1, wherein the one or more *Toxocara* roundworm antigens is *Toxocara canis* antigen or *Toxocara cati* antigen.

12. A device for determining the presence or absence of an intestinal *Toxocara* roundworm infection in a mammal, the device comprising a solid support, wherein one or more antibodies specific for one or more *Toxocara* roundworm coproantigens are immobilized on the solid support.

13. The device of claim 12 wherein the one or more antibodies specific for one or more *Toxocara* roundworm coproantigens are not specific for any coproantigen from the mammal selected from the group consisting of hookworm, whipworm, and heartworm.

14. The device of claim 12 wherein the one or more antibodies are specific for an extract of whole *Toxocara* roundworm, an extract of *Toxocara* roundworm intestine or an extract of *Toxocara* roundworm reproductive organ.

15. The device of claim 12 wherein the *Toxocara* roundworm is *Toxocara canis*.

16. The device of claim 12 wherein one or more of the one or more antibodies are specifically bound to one or more *Toxocara* roundworm coproantigens.

17. The device of claim 12 wherein one or more of the one or more antibodies are labeled.

18. The device of claim 12 wherein the device is an enzyme-linked immunosorbent assay device.

19. The device of claim 18 wherein the enzyme-linked immunosorbent assay device is a lateral flow immunoassay device.

20. The device of claim 12 wherein the mammal is a canine or a feline.

21. The device of claim 12, wherein the one or more *Toxicara* roundworm coproantigens are *Toxocara canis* or *Toxocara cati* coproantigens.

22. A kit for detection of one or more *Toxocara* roundworm antigens in a sample of a mammal, the kit comprising the device of any one of claims 1-11 and 12-21, and one or more reagents sufficient for the detection of the one or more *Toxocara* roundworm antigens.

23. The kit of claim 22 wherein the one or more reagents are selected from the group consisting of one or more indicator reagents, one or more antibody labeling compounds, one or more enzyme substrates, one or more antibodies specific for one or more *Toxocara* roundworm antigens, one or more anti-species antibodies, one or more antigen capture reagents, one or more inhibitors, and one or more wash reagents.

24. The kit of claim 22 wherein the one or more *Toxocara* roundworm antigens are *Toxocara* roundworm coproantigens.

25. The device of claim 1 wherein the one or more *Toxocara* roundworm antigens are *Toxocara* roundworm coproantigens.

* * * * *